United States Patent
Torita et al.

(10) Patent No.: US 10,588,726 B2
(45) Date of Patent: Mar. 17, 2020

(54) DENTAL MILL BLANK WITH INTERMEDIATE COLOR LAYER AT 30% POSITION

(71) Applicant: SHOFU INC., Kyoto (JP)

(72) Inventors: Yasuhiro Torita, Kyoto (JP); Yusei Kadobayashi, Kyoto (JP)

(73) Assignee: SHOFU INC., Kyoto (JP)

( * ) Notice: Subject to any disclaimer, the term of this patent is extended or adjusted under 35 U.S.C. 154(b) by 138 days.

(21) Appl. No.: 15/627,690

(22) Filed: Jun. 20, 2017

(65) Prior Publication Data

US 2018/0147034 A1    May 31, 2018

(30) Foreign Application Priority Data

Nov. 28, 2016  (JP) ................................ 2016-229810

(51) Int. Cl.
*A61C 13/00*  (2006.01)
*A61C 5/77*  (2017.01)
*A61C 13/09*  (2006.01)
*A61C 13/08*  (2006.01)

(52) U.S. Cl.
CPC ............ *A61C 13/0022* (2013.01); *A61C 5/77* (2017.02); *A61C 13/082* (2013.01); *A61C 13/09* (2013.01)

(58) Field of Classification Search
CPC . A61C 13/0004; A61C 13/09; A61C 13/0029; A61C 13/082; A61C 5/08; A61C 5/10; A61C 5/77; A61C 13/0022
USPC ....................................................... 433/218
See application file for complete search history.

(56) References Cited

U.S. PATENT DOCUMENTS

| | | |
|---|---|---|
| 2003/0207235 A1 | 11/2003 | der Zel |
| 2014/0328746 A1 | 11/2014 | Yamada et al. |
| 2014/0377718 A1* | 12/2014 | Korten ............... A61C 13/0022 433/218 |
| 2016/0228222 A1 | 8/2016 | Rolf et al. |

FOREIGN PATENT DOCUMENTS

| | | | |
|---|---|---|---|
| JP | 2012-087086 | 5/2012 | |
| JP | 2014-218389 | * 11/2014 | ............. C04B 35/48 |
| JP | 2014-218418 | * 11/2014 | ............. C04B 35/48 |

OTHER PUBLICATIONS

Notification of Reasons for Refusal dated Jan. 25, 2017 in corresponding Japanese Patent Application No. 2016-229810 with English Translation.
Extended European Search Report dated Feb. 20, 2018 in corresponding European Patent Application No. 17176879.9.

\* cited by examiner

*Primary Examiner* — Khanh T Nguyen
(74) *Attorney, Agent, or Firm* — Wenderoth, Lind & Ponack, L.L.P.

(57) ABSTRACT

A dental mill blank having a multi-layer structure has been required to improve the reproducibility of a color tone of the natural tooth in a dental crown restoration cut by CAD/CAM technique. Especially, a reproduction of the color tone of a cavity or a groove is required in a dental crown form of the molar tooth. The present dental mill blank has three or more layers wherein a color of a 30% position layer which includes a 30% position which is a position spaced from a surface of the dental mill blank of a W layer-side by 30% satisfies a specified relational expression, and a contrast ratio of the 30% position layer is within a range of the contrast ratio of the D layer×(0.70 to 1.00).

4 Claims, 3 Drawing Sheets

DENTAL MILL BLANK WITH INTERMEDIATE COLOR LAYER AT 30% POSITION

CROSS-REFERENCE TO RELATED APPLICATIONS

This application is based on and claims the benefit of priority from Japanese Patent Application Serial No. 2016-229810 (filed on Nov. 28, 2016), the contents of which are hereby incorporated by reference in their entirety.

BACKGROUND OF THE INVENTION

Field of the Invention

The present disclosure relates to a dental mill blank for CAD/CAM having a multi-layer structure used in a dental field, and, more particularly to a dental mill blank for CAD/CAM having a color tone structure in a specific layer.

Description of the Related Art

In the dental field, a method of preparing of a dental crown restoration by cutting a block or a disk which are mill blanks using CAD/CAM technique is known. In recent years, in order to approximate a color tone of a dental crown restoration prepared by cutting and machining using the CAD/CAM technique to the color tone of the natural teeth, a mill blank having a multi layered structure in which a plurality of materials having different color tones are stacked in a layer form, in the dental field is used in the dental field.

Specifically, the feature of the mill blank having the multi layered structure is that a plurality of layers having different color tones, different transparencies, different materials or the like are stacked in various thickness.

When a dental crown restoration is cut from a conventional mill blank having a multi layered structure, a positional relationship of the multi layered structure is not appropriate. Therefore, it has been impossible that the dental crown restoration is positioned in a positional relationship which may optimize reproduction of a color tone in cavity or the like. Thus, because an appropriate color tone is not reproduced in a conventional dental crown restoration, it has been difficult to reproduce a color tone of the natural tooth.

Patent Literatures 1 and 2 disclose that a relationship of a color in each layer is defined in order to reproduce a color tone of the natural tooth in a dental mill blank having a plurality of parallel layers. However, a relationship of a color distribution is not appropriate. Therefore, a technique for reproducing a color tone of the natural teeth have been required.

RELEVANT REFERENCES

List of Relevant Patent Literature

Patent Literature 1: Japanese Unexamined Patent Application Publication No. 2014-218389
Patent Literature 2: Japanese Unexamined Patent Application Publication No. 2014-218418

SUMMARY OF THE INVENTION

Technical Problem

A dental mill blank having a multi-layer structure has been required to improve the reproducibility of a color tone of the natural tooth in a dental crown restoration cut by CAD/CAM technique. Especially, a reproduction of a color tone of a cavity or a groove is required in a dental crown form of the molar tooth.

In the natural tooth, because the enamel in the cavity or in the groove is thin, the color tone of the dentin is reflected on the outside via the enamel. Therefore, a color of the cavity or the groove looks like deeper than a color of the dental cusp. Especially, not only the enamels of a mesial fovea, a central fovea and a distal fovea are thin, but also the mesial fovea, the central fovea and the distal fovea are often soiled by stain and the like. Therefore the mesial fovea, the central fovea and the distal fovea express more dark color tone. In addition, the color tone of the dentin is reflected in a central groove and a sub groove following a mesial fovea and a distal fovea, and the central groove and the sub groove are often soiled by stain and the like. Therefore, the central groove and the sub groove express more dark color tone.

On the other hand, the enamel in the dental cusp is thick, therefore the color tone of the dentin is hardly reflected on the dental cusp. Further, there are many cases where the dental cusp loses transparency to become white by phenomena such as the whitening.

Thus, the technique which easily and appropriately reproduce the color tone of the various natural tooth have been required.

Solution to Problem

The present disclosure provides a dental mill blank including three or more layers which are stacked on each other, wherein in a case in which a chromaticity of each layer based on the $L^*a^*b^*$ colorimetric system is expressed by $\sqrt{(L^{*2} \times a^{*2} \times b^{*2})}$, a layer which has the highest chromaticity is defined as a W layer (chromaticities in the W layer based on the $L^*a^*b^*$ colorimetric system: WL, Wa, Wb), and a layer which has the lowest chromaticity is defined as a D layer (chromaticities in the D layer based on the $L^*a^*b^*$ colorimetric system: DL, Da, Db), the W layer and the D layer are respectively disposed on opposed surface layers of the dental mill blank, that is, on surface layers of substantially parallel layers, and a color of a 30% position layer (chromaticities in the 30% position layer based on the $L^*a^*b^*$ colorimetric system: 30% position L, 30% position a, 30% position b) which includes a position spaced from a surface of the dental mill blank of a W layer-side by 30% of a dimension between the surface of the dental mill blank of a W layer-side and the surface of the dental mill blank of a D layer-side (when a boundary of the layers is positioned at the position spaced from the surface of the dental mill blank of the W layer-side by 30%, the 30% position layer includes a position exceeding the position spaced from the surface of the dental mill blank of the W layer-side by 30%) satisfies the following relations:

30% position $L$ is within a range of $((WL+DL)/2) \times (0.90 \text{ to } 1.10)$ 30% position $a$ is within a range of $((Wa+Da)/2) \times (0.90 \text{ to } 1.10)$, and 30% position $b$ is within a range of $((Wb+Db)/2) \times (0.90 \text{ to } 1.10)$.

In the present disclosure, it is preferable that the color of a 30% position layer satisfies the following relations:

30% position L is within a range of $((WL+DL)/2) \times (0.95 \text{ to } 1.05)$ 30% position a is within a range of $((Wa+Da)/2) \times (0.95 \text{ to } 1.05)$, and 30% position b is within a range of $((Wb+Db)/2) \times (0.95 \text{ to } 1.05)$.

In the present disclosure, when a boundary of the layers is positioned at the position spaced from the surface of the dental mill blank of the W layer-side by 30%, the 30% position layer is a layer which is adjacent to the boundary at a position exceeding the position spaced from the surface of the dental mill blank of the W layer-side by 30%. That is, in the present disclosure, when a boundary of the layers is positioned at the position spaced from the surface of the dental mill blank of the W layer-side by 30%, the 30% position layer is a layer which includes a position which is adjacent to the boundary at a position exceeding the position spaced from the surface of the dental mill blank of the W layer-side by 30%. In addition, when the W layer includes a position spaced from a surface of the dental mill blank of a W layer-side by 30%, the 30% position layer is a layer which is adjacent to the W layer.

Further, in the present disclosure, "$\sqrt{(L^{*2} \times a^{*2} \times b^{*2})}$" means "$(L^{*2} \times a^{*2} \times b^{*2})^{1/2}$".

In a dental mill blank of the present disclosure, a contrast ratio of the D layer is within a range of 0.55 to 0.95, and a contrast ratio of the 30% position layer is within a range of the contrast ratio of the D layer×(0.70 to 1.00). It is preferable that the contrast ratio of the 30% position layer is within a range of 0.50 to 0.95. In the present disclosure, a contrast ratio of the W layer is preferably 0.90 or less, more preferably within a range of 0.30 to 0.90, and further more preferably within a range of 0.30 to 0.54 or a range of 0.70 to 0.85.

In the present disclosure, the W layer is preferably positioned from the surface of the dental mill blank to at least a position spaced from the surface of the dental mill blank by 15 to 30%, and more preferably 25 to 30%, of the dimension between the opposed surfaces of the dental mill blank.

In the present disclosure, it is preferable that a thickness of the 30% position layer is within a range of 10 to 20% of the dimension between the opposed surfaces of the dental mill blank. In the present disclosure, it is preferable that the 30% position layer is positioned adjacent to the W layer. In the present disclosure, "30% position layer is positioned adjacent to the W layer" includes not only the case the W layer and the 30% position layer are directly adjacent each other but also the case an adhesion layer having the thickness which does not inhibit aesthetic properties such as 200 µm or less is provided between the W layer and the 30% position layer.

In the present disclosure, a dental mill blank may have a G layer which is a new layer in order to impart gradation. It is preferable that the G layer has 1 to 3 layer(s) (G1 layer, G2 layer, G3 layer). It is most preferable that the G layer has 2 layers (G1 layer, G2 layer). It is preferable that the thickness of each layer which constitutes the G layer is thinner than the thickness of the D layer. Further, in a case in which a chromaticity of each G layer based on the L*a*b* colorimetric system is expressed by $\sqrt{(L^{*2} \times a^{*2} \times b^{*2})}$, chromaticities of the layer constituting the G layer (G1 layer, G2 layer, G3 layer . . . ) preferably satisfies the following relations with the approach to the D layer from the 30% position layer:

30% position layer $\sqrt{(L^{*2} \times a^{*2} \times b^{*2})}$ < G1 layer < G2 layer < G3 layer . . . < D layer $\sqrt{(L^{*2} \times a^{*2} \times b^{*2})}$ In the present disclosure, as to a color relationship of the layers in the dental mill blank, it is preferable that the increase-decrease tendency of the chromaticities based on the L*a*b* colorimetric system from the W layer to the D layer is not varied.

Furthermore, one example of color relationship of the layers includes
WL is within a range of 68.8 to 87.2
Wa is within a range of −3.1 to 4.8
Wb is within a range of −2.9 to 19.0
DL is within a range of 55.0 to 79.0
Da is −4.6 or more
Db is 29.3 or less
30% position L is within a range of 61.9 to 83.1
30% position a is −3.85 or more
30% position b is within a range of 2.7 to 24.15
DL<30% position L<WL
Da<30% position a<Wa and
Db>30% position b>Wb.

It is preferable that Da is 4.6 or less. It is preferable that Db is 2.8 or more. It is preferable that 30% position a is 4.7 or less.

Advantageous Effects of Invention

In a dental mill blank of the present disclosure, a color of the natural tooth may be reproduced by a color tone of a cut dental crown restoration and a transparency similar to the natural tooth may be reproduced. Therefore, the dental crown may be aesthetically designed in the dental mill blank.

Especially, in the dental crown form of a molar tooth, a color tone of the occlusal plane view which is in a field of view when an oral cavity is observed from the outside may be reproduced. In the occlusal plane view, a color tone of a cavity may be appropriately reproduced.

DETAILED DESCRIPTION OF THE PREFERRED EMBODIMENTS

Now a specific description of the present disclosure is given.

The present inventors have found that it is suitable for reproducing the natural tooth color by the color tone of the cut dental crown restoration that a layer having (WL+DL)/2, (Wa+Da)/2 and (Wb+Db)/2 which are mean values of the color tones of the W layer and the color tones of the D layer which are L*a*b* values based on the L*a*b* colorimetric system is positioned at a position spaced from a surface of the dental mill blank of a W layer-side by 30% (or at a position which exceeds the position spaced from the surface of the dental mill blank of the W layer-side by 30% when a boundary of the layers is positioned at the position spaced from the surface of the dental mill blank of the W layer-side by 30%). Further, the present inventors have found that transparency similar to the natural tooth is reproduced by a contrast ratio of the D layer within a range of 0.55 to 0.95 and a contrast ratio of the 30% position layer within a range of the contrast ratio of the D layer×(0.70 to 1.00). The present invention is based on this knowledge.

A material of a dental mill blank of the present disclosure is not limited particular, and any materials such as a resin material, an inorganic material, and a composite material may be used as the material of a dental mill blank of the present disclosure. Preferable resin materials include an acrylic resin material, preferable inorganic materials include an aluminosilicate glass, zirconia and alumina, and preferable composite materials include a mixed material of an acrylic resin material and an inorganic powder.

A dental mill blank of the present disclosure is a molded body for cutting out a dental crown restoration by using a CAD/CAM technique. More specifically, examples thereof include: a block in the shape of a rectangular prism formed to have a dimension of 1 to 2 cm by 1 to 2 cm by 2 to 3 cm (height); a rectangular prism formed to have a dimension of 1 to 3 cm (height) by 6 to 15 cm (one side) by 6 to 15 cm (one side); and a cylindrical disc formed to have a dimension of 1 to 3 cm (height) by 6 to 15 cm (diameter).

A dental mill blank of the present disclosure may be prepared by molding a plurality of stacked layers having different color tones from each other, and may have 3 or more layers, for example, may have 3 to 8 layers. Among them, it is preferable that a dental mill blank has a three layers consisting of an enamel color layer, a dentin color layer and a cervical area color layer, and it is more preferable that a dental mill blank consists of a three layers structure including an enamel color layer, a dentin color layer and a cervical area color layer.

It is more preferable that a dental mill blank has a five layers structure consisting of an enamel color layer, a dentin color layer, a cervical area color layer, an intermediate color layer which has an intermediate color of an enamel color and a dentin color and is provided between the enamel color layer and the dentin color layer, and an intermediate color layer which has an intermediate color of the dentin color and a cervical area color and is provided between the dentin color layer and the cervical area color layer. In the present disclosure, a layer having the thickness of 200 μm or less such as an adhesion layer is not counted as the layer constituting the dental mill blank.

In a case in which a chromaticity of each layer based on the $L^*a^*b^*$ colorimetric system is expressed by $\sqrt{(L^{*2} \times a^{*2} \times b^{*2})}$, when a layer which has the highest chromaticity is defined as a W layer and a layer which has the lowest chromaticity is defined as a D layer, the W layer may be positioned on a surface of the dental mill blank and may have an enamel color, and the D layer may be positioned on a surface opposing to the surface on which W layer is positioned and may have a cervical area color layer.

The W layer has an enamel layer, and when chromaticities in the W layer based on the $L^*a^*b^*$ colorimetric system are expressed by WL, Wa, Wb, it is preferable that WL is within a range of 68.8 to 87.2, Wa is within a range of −3.1 to 4.8, and Wb is within a range of −2.9 to 19.0.

The D layer which has a cervical area color layer is positioned on the end layer opposing to the layer having the enamel color, and when chromaticities in the D layer based on the $L^*a^*b^*$ colorimetric system are expressed by DL, Da, Db, it is preferable that DL is within a range of 55.0 to 79.0, Da is −4.6 or more, and Db is 29.3 or less. It is more preferable that Da is 10.6 or less, and Db is 2.5 or more.

The 30% position layer includes a position spaced from a surface of the dental mill blank of a W layer-side toward the D layer by 30% of a dimension between the surface of the dental mill blank of a W layer-side and the surface of the dental mill blank of a D layer-side. When chromaticities in the 30% position layer based on the $L^*a^*b^*$ colorimetric system is expressed by 30% position L, 30% position a, 30% position b, 30% position L is within a range of $((WL+DL)/2) \times (0.90$ to $1.10)$, 30% position a is within a range of $((Wa+Da)/2) \times (0.90$ to $1.10)$, and 30% position b is within a range of $((Wb+Db)/2) \times (0.90$ to $1.10)$. It is preferable that 30% position L is within a range of $((WL+DL)/2) \times (0.95$ to $1.05)$, 30% position a is within a range of $((Wa+Da)/2) \times (0.95$ to $1.05)$, and 30% position b is within a range of $((Wb+Db)/2) \times (0.95$ to $1.15)$.

In the present disclosure, it is preferable that the relations DL<30% position L<WL, Da<30% position a<Wa, and, Db>30% position b>Wb are satisfied.

For measurement of the chromaticities based on the $L^*a^*b^*$ colorimetric system, each layer in the dental mill blank of the present disclosure is molded into a disc of 15 mm in diameter and 1.0 mm in thickness, and the molded body is sintered and/or cured appropriately, and both faces of the molded body is polished smooth. A device for measurement of the chromaticities, manufactured by Olympus Corporation under the trade name of CE100-DC/US, is used for measurement. The condition of measurement of the chromaticities is as follow: Light source: C light source, Angle of visibility: 2°, Background color: White. The number of the specimen of measurement of the chromaticities is 5 and the chromaticities are evaluated by the average.

Next, a description of the contrast ratio is given.

A contrast ratio is a measure of representing a transparency. A contrast ratio is calculated from Y value of XYZ color system which is defined in JIS Z8701. Among the tristimulus values, Y relates to brightness. Specifically, the sample plate with a thickness of 1.0 mm are placed on a black or white background. The standard light C is irradiated and the Y value of the reflected light is measured. When the background is black, the Y is referred to Yb. When the background is white, the Y is referred to Yw. The contrast ratio (C) is obtained from Yb/Yw. When the C value is close to 1, the materials are opaqueness. When the C value is close to zero, the materials are transparency.

In the present disclosure, a contrast ratio of the D layer is within a range of 0.55 to 0.95, and is preferably selected from a range of 0.55 to 0.75, and is more preferably selected from a range of 0.57 to 0.70. Further, the contrast ration of the W layer is preferably 0.90 or less, is more preferably within a range of 0.30 to 0.90, is further preferably selected from a range of 0.30 to 0.54 or a range of 0.70 to 0.85, and is most preferably selected from a range of 0.35 to 0.52. It is preferable that the D layer and the W layer have different transparencies each other. More specifically, the difference of the contrast ratio (the value obtained by subtracting the value of the W layer from the value of the D layer) is preferably within a range of 0.05 to 0.40, and is more preferably within the range of 0.10 to 0.30. When the contrast ratio is within the range, the transparencies well adapt to the transparencies of the enamel and the dentin.

In the present disclosure, a contrast ratio of the 30% position layer is within a range of the contrast ratio of the D layer×(0.70 to 1.00), and is preferably within a range of the contrast ratio of the D layer×(0.50 to 0.95).

In a dental mill blank of the present disclosure, it is preferable that each layer is stacked and molded in such a way that boundaries of each layer is substantially parallel each other, and it is more preferable that each layer is stacked and molded in such a way that boundaries of each layer is parallel each other. In a dental mill blank of the present disclosure, each layer may have a curved surface to be stacked and molded without any problems. In this case, a surface opposing to an adjacent layer in each layer preferably has a shape which is similar to a shape of surface opposing to the adjacent layer in other layer. Further, when a pair of opposed surfaces of the layer are adjacent to other layers, it is preferable that the pair of opposed surfaces have a similar shape each other. In the present disclosure, in the case that layers having a curved surface are stacked and molded, the position spaced from a surface of the dental mill blank of a W layer-side by 30% (30% position) is determined by a perpendicular line to the surface of the W layer from the center of the gravity. The reason is that a cavity of a dental crown is positioned in the neighborhood of this portion when a dental crown form is cut.

Next, a specific description is given with reference to the drawings.

Figure 1:
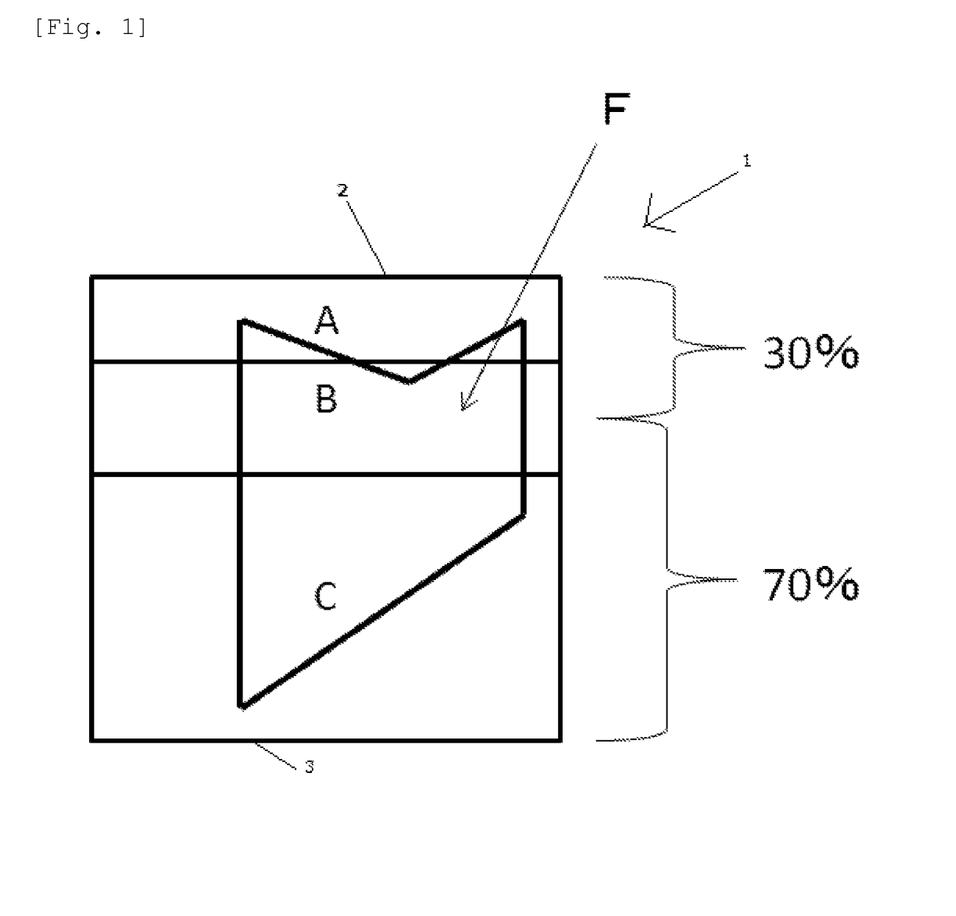
FIG. 1 is a schematic sectional view of a dental mill blank of the present disclosure represented by three layers cut on a coronal surface vertical to the apical and the cervical at a position of a cavity of a dental crown form to be cut.
Figure 2:
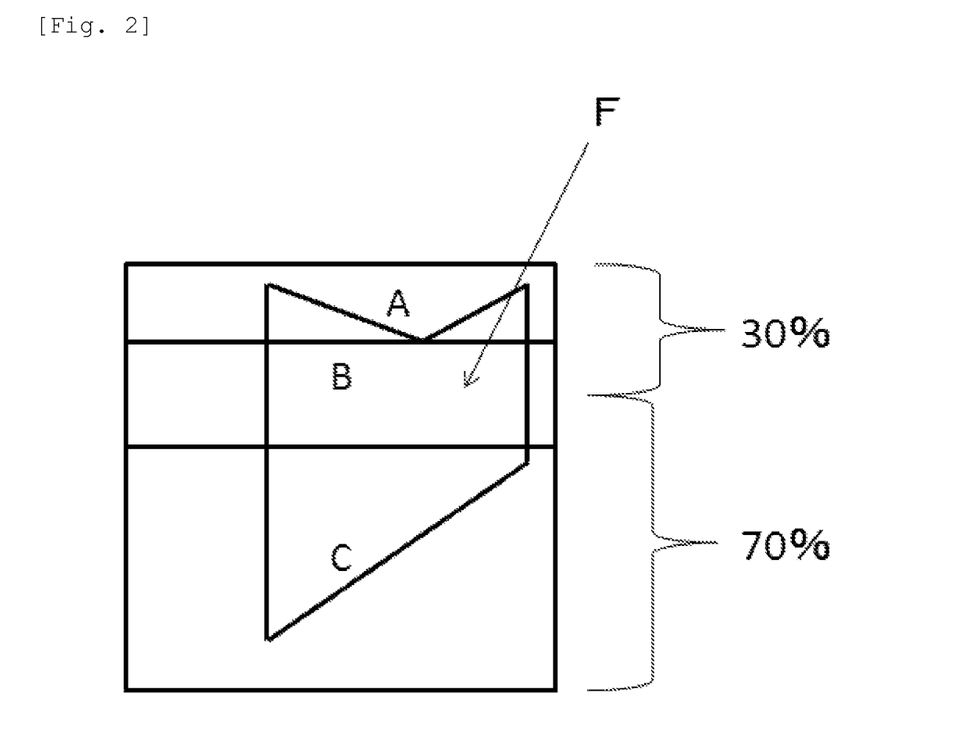
FIG. 2 is a schematic view of the dental mill blank shown in FIG. 1 in which a dental crown form is designed in the A layer-side.
Figure 3:
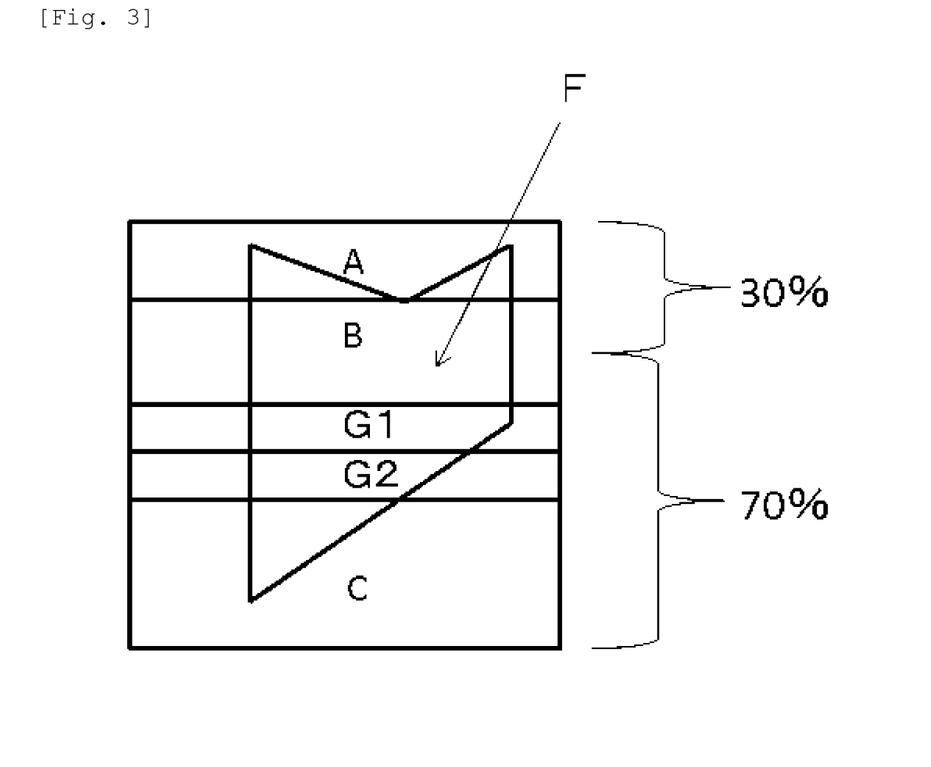
FIG. 3 is a schematic view of a dental mill blank having gradation layers (G1 and G2) between a 30% position layer and a D layer.

FIG. 1 shows a schematic view of a dental mill blank of one embodiment of the present disclosure. FIG. 2 shows a schematic view of a dental mill blank in which a dental crown shape is positioned close to an A layer. FIG. 3 shows a schematic view of a dental mill blank having gradation layers (G1 and G2) between a 30% position layer and a D layer.

A dental mill blank 1 shown in FIG. 1 consists of three layers including an A layer, a B layer and a C layer. The A layer corresponds to the W layer and has an enamel color. The C layer corresponds to the D layer and has a cervical area color. In the dental mill blank 1 shown in FIG. 1, the B layer includes a position spaced from a surface 2 of the dental mill blank of the side of the A layer which corresponds to the W layer toward the C layer which corresponds to the D layer by 30% of a dimension between the surface 2 of the dental mill blank of the W layer-side and the surface 3 of the dental mill blank of the D layer-side. The A layer which corresponds to the W layer is preferably positioned from the surface 2 of the dental mill blank of a W layer-side to a position spaced from the surface 2 of the dental mill blank of the W layer-side by 15 to 30% of the dimension between the surface 2 of the dental mill blank of the W layer-side and the surface 3 of the dental mill blank of the D layer-side. The thickness of the 30% position layer which corresponds to the B layer is preferably within a range of 10 to 20% of the dimension between the surface 2 of the dental mill blank of the W layer-side and the surface 3 of the dental mill blank of the D layer-side.

The dental mill blank 1 may include many layers other than the above described layers without any problems. That is, the dental mill blank 1 may include a different layer other than A layer, B layer and C layer between A layer and B layer and/or B layer and C layer.

When a boundary of the layers is positioned at the position spaced from the surface of the dental mill blank of the W layer-side by 30%, the B layer may be positioned at a position which is adjacent to the boundary and exceeds the position spaced from the surface of the dental mill blank of the W layer-side by 30%.

Therefore, a boundary of the A layer and the B layer is preferably positioned at the position spaced from a surface 2 of the dental mill blank of the A layer toward a surface 3 of the C layer by 30% or at a position not exceeding the position spaced from a surface 2 of the dental mill blank of the A layer toward a surface 3 of the C layer by 30%. In this case, the boundary of the A layer and the B layer is more preferably positioned at a position which exceeds a position spaced from a surface 2 of the dental mill blank of the A layer toward a surface 3 of the C layer by 15%.

Further, it is preferable that a boundary the B layer and the C layer is preferably positioned at a position exceeding a position spaced from a surface 2 of the dental mill blank of the A layer toward a surface 3 of the C layer by 30%. In this case, the boundary of the B layer and the C layer is more preferably positioned at a position exceeding a position spaced from a surface 2 of the dental mill blank of the A layer toward a surface 3 of the C layer by 40%.

The thicknesses of the A layer, the B layer and the C layer in the direction from the surface 2 of the A layer toward the surface 3 of the C layer of the dental mill blank is preferably 15% or more of the dimension between the surface of the dental mill blank of a W layer-side and the surface of the dental mill blank of a D layer-side.

In the Drawings, a dental crown form to be cut out is shown by F. A dental cups portion is formed in the A layer which is an enamel color portion, and a cavity portion is formed in the B layer. Therefore, when the dental crown is observed from the occlusal plane view, the color tone changes to improve aesthetic properties. Further, as shown in FIGS. 2 and 3, the dental cups portion is formed in the A layer which is an enamel color portion and the cavity portion is formed in the vicinity of boundary of the A layer and the B layer. Therefore, the B layer may be seen through the thin A layer to improve aesthetic properties. More aesthetic dental crown restoration may be obtained by forming the layers according to the present disclosure.

EXAMPLES

Hereinafter, the present disclosure is described by way of Examples in more detail, and specifically, but the present disclosure is not limited to these Examples.

(Measurement of Chromaticity and Contrast Ratio)

The uncured paste-like substances to be used for the respective layers of each Example were filled in a $\phi$15 mm×1.2 mm die, polymerized and cured. The disk-like product after molding was regulated so as to have a thickness of 1.0 mm with water-resistant polishing paper, and the surface of the disk-like product was finish-polished by buffing. The disk-like product after polishing was subjected to the measurement of the $L^*a^*b^*$ value over a white background by using a spectrocolorimeter (CM-3500d: Konica Minolta). The same measurement was performed over a black background, and from the Y value (YW) of white background colorimetry and the Y value (YB) of black background colorimetry, YB/YW was defined as the contrast ratio.

(Evaluation of Color Tone of Prosthetic Device)

A molded block body was milled and machined by using a dental CAD/CAM milling and machining machine DWX-50 (Roland) to prepare a crown for a right first premolar of lower jaw. The prepared crown was visually observed by 10 persons, and the evaluation of the color tone of the prosthetic device was performed by evaluating the color tone reproducibility and the transparency reproducibility as a dental crown prosthetic device. In Tables, the evaluation in the column of "Evaluation Result" are as follows: the case where 10 visual observers in the 10 visual observers gave the evaluation that the color tone reproducibility was satisfactory is represented by "AA: the color tones is perfectly reproduced"; the case where nine observers gave the foregoing evaluation is represented by "A: the color tone reproducibility is extremely satisfactory"; the case where eight or seven observers gave the foregoing evaluation is represented by "B: the color tone reproducibility is good"; and the case where six or less observers gave the foregoing evaluation is represented by "C: the color reproducibility is poor."

(Preparation of Pastes)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.3 part by weight of benzoyl peroxide: BPO. To 40 parts by weight of the polymerizable monomer liquid mixture, 60 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance. By varying the mixing amounts of the respective colorants, paste-like substances each having a transparency and a desired color tone in each layer which constitutes the dental mill blank in each Examples and Comparative Examples were prepared.

(Preparation of Block Bodies)

In a 12×14×18 mm die for preparing a block body, a paste-like substance for the lowermost layer (D layer), a paste-like substance for the 30% position layer and a paste-like substance for the uppermost layer (W layer) are filled in the thickness described in Examples and Comparative Examples. The die was heated to 100° C., the paste-like substances were polymerized and cured to yield a block body having a three-layer structure. Tables of Examples describe the measured chromaticities and the measured contrast ratios of the used paste-like substances.

TABLE 1

| | | Example 1 | Example 2 | Example 3 | Comparative Example 1 | Comparative Example 2 | Example 4 | Example 5 | Comparative Example 3 | Comparative Example 4 |
|---|---|---|---|---|---|---|---|---|---|---|
| A layer (W layer) | L* (WL) | 78.00 | 78.00 | 78.00 | 78.00 | 78.00 | 78.00 | 78.00 | 78.00 | 78.00 |
| | a* (Wa) | 3.00 | 3.00 | 3.00 | 3.00 | 3.00 | 3.00 | 3.00 | 3.00 | 3.00 |
| | b* (Wb) | 8.05 | 8.05 | 8.05 | 8.05 | 8.05 | 8.05 | 8.05 | 8.05 | 8.05 |
| | Contrast Ratio | 0.42 | 0.42 | 0.42 | 0.42 | 0.42 | 0.42 | 0.42 | 0.42 | 0.42 |
| | Thickness | 2.0 mm | 2.0 mm | 2.0 mm | 2.0 mm | 2.0 mm | 2.0 mm | 2.0 mm | 2.0 mm | 2.0 mm |
| C Layer (D layer) | L* (DL) | 67.00 | 55.00 | 60.00 | 55.00 | 60.00 | 67.00 | 67.00 | 67.00 | 67.00 |
| | a* (Da) | 0.85 | 0.85 | 0.85 | 0.85 | 0.85 | −4.60 | 10.60 | −4.60 | 10.60 |
| | b* (Db) | 15.90 | 15.90 | 15.90 | 15.90 | 15.90 | 15.90 | 15.90 | 15.90 | 15.90 |
| | Contrast Ratio | 0.75 | 0.75 | 0.75 | 0.75 | 0.75 | 0.75 | 0.75 | 0.75 | 0.75 |
| | Thickness | 6.5 mm | 6.5 mm | 6.5 mm | 6.5 mm | 6.5 mm | 6.5 mm | 6.5 mm | 6.5 mm | 6.5 mm |
| B layer (30% position layer) | L* | 72.50 | 59.85 | 75.90 | 58.52 | 77.28 | 72.50 | 72.50 | 72.50 | 72.50 |
| | a* | 1.93 | 1.93 | 1.93 | 1.93 | 1.93 | −0.72 | 7.48 | −0.70 | 7.62 |
| | b* | 11.98 | 11.98 | 11.98 | 11.98 | 11.98 | 11.98 | 11.98 | 11.98 | 11.98 |
| | Contrast Ratio | 0.64 | 0.64 | 0.64 | 0.64 | 0.64 | 0.64 | 0.64 | 0.64 | 0.64 |
| | Thickness | 1.5 mm | 1.5 mm | 1.5 mm | 1.5 mm | 1.5 mm | 1.5 mm | 1.5 mm | 1.5 mm | 1.5 mm |
| | Evaluation Result | AA | A | AA | C | C | AA | A | C | C |

TABLE 2

| | | Example 6 | Example 7 | Comparative Example 5 | Comparative Example 6 | Example 8 | Example 9 | Comparative Example 7 | Comparative Example 8 |
|---|---|---|---|---|---|---|---|---|---|
| A layer (W layer) | L* (WL) | 78.00 | 78.00 | 78.00 | 78.00 | 78.00 | 78.00 | 78.00 | 78.00 |
| | a* (Wa) | 3.00 | 3.00 | 3.00 | 3.00 | 3.00 | 3.00 | 3.00 | 3.00 |
| | b* (Wb) | 8.05 | 8.05 | 8.05 | 8.05 | 8.05 | 8.05 | 8.05 | 8.05 |
| | Contrast Ratio | 0.42 | 0.42 | 0.42 | 0.42 | 0.30 | 0.54 | 0.20 | 0.60 |
| | Thickness | 2.0 mm | 2.0 mm | 2.0 mm | 2.0 mm | 2.0 mm | 2.0 mm | 2.0 mm | 2.0 mm |
| C Layer (D layer) | L* (DL) | 67.00 | 67.00 | 67.00 | 67.00 | 67.00 | 67.00 | 67.00 | 67.00 |
| | a* (Da) | 0.85 | 0.85 | 0.85 | 0.85 | 0.85 | 0.85 | 0.85 | 0.85 |
| | b* (Db) | 2.50 | 29.30 | 2.50 | 29.30 | 15.90 | 15.90 | 15.90 | 15.90 |
| | Contrast Ratio | 0.75 | 0.75 | 0.75 | 0.75 | 0.75 | 0.75 | 0.75 | 0.75 |
| | Thickness | 6.5 mm | 6.5 mm | 6.5 mm | 6.5 mm | 6.5 mm | 6.5 mm | 6.5 mm | 6.5 mm |
| B layer (30% position layer) | L* | 72.50 | 72.50 | 72.50 | 72.50 | 72.50 | 72.50 | 72.50 | 72.50 |
| | a* | 1.93 | 1.93 | 1.93 | 1.93 | 1.93 | 1.93 | 1.93 | 1.93 |
| | b* | 4.75 | 20.54 | 4.64 | 20.92 | 11.98 | 11.98 | 11.98 | 11.98 |
| | Contrast Ratio | 0.64 | 0.64 | 0.64 | 0.64 | 0.64 | 0.64 | 0.64 | 0.64 |
| | Thickness | 1.5 mm | 1.5 mm | 1.5 mm | 1.5 mm | 1.5 mm | 1.5 mm | 1.5 mm | 1.5 mm |
| | Evaluation Result | A | AA | C | C | AA | AA | C | C |

TABLE 3

| | | Example 10 | Example 11 | Comparative Example 9 | Comparative Example 10 | Example 12 | Example 13 | Comparative Example 11 | Comparative Example 12 | Example 14 | Example 15 |
|---|---|---|---|---|---|---|---|---|---|---|---|
| A layer (W layer) | L* (WL) | 78.00 | 78.00 | 78.00 | 78.00 | 78.00 | 78.00 | 78.00 | 78.00 | 78.00 | 78.00 |
| | a* (Wa) | 3.00 | 3.00 | 3.00 | 3.00 | 3.00 | 3.00 | 3.00 | 3.00 | 3.00 | 3.00 |
| | b* (Wb) | 8.05 | 8.05 | 8.05 | 8.05 | 8.05 | 8.05 | 8.05 | 8.05 | 8.05 | 8.05 |
| | Contrast Ratio | 0.42 | 0.42 | 0.42 | 0.42 | 0.42 | 0.42 | 0.42 | 0.42 | 0.42 | 0.42 |
| | Thickness | 2.0 mm | 2.0 mm | 2.0 mm | 2.0 mm | 2.0 mm | 2.0 mm | 2.0 mm | 2.0 mm | 2.0 mm | 2.0 mm |
| C Layer (D layer) | L* (DL) | 67.00 | 67.00 | 67.00 | 67.00 | 67.00 | 67.00 | 67.00 | 67.00 | 67.00 | 67.00 |
| | a* (Da) | 0.85 | 0.85 | 0.85 | 0.85 | 0.85 | 0.85 | 0.85 | 0.85 | 0.85 | 0.85 |
| | b* (Db) | 15.90 | 15.90 | 15.90 | 15.90 | 15.90 | 15.90 | 15.90 | 15.90 | 15.90 | 15.90 |
| | Contrast Ratio | 0.55 | 0.95 | 0.50 | 0.99 | 0.75 | 0.75 | 0.75 | 0.75 | 0.55 | 0.95 |
| | Thickness | 6.5 mm | 6.5 mm | 6.5 mm | 6.5 mm | 6.5 mm | 6.5 mm | 6.5 mm | 6.5 mm | 6.5 mm | 6.5 mm |

TABLE 3-continued

|  |  | Example 10 | Example 11 | Comparative Example 9 | Comparative Example 10 | Example 12 | Example 13 | Comparative Example 11 | Comparative Example 12 | Example 14 | Example 15 |
|---|---|---|---|---|---|---|---|---|---|---|---|
| B layer (30% position layer) | L* | 72.50 | 72.50 | 72.50 | 72.50 | 72.50 | 72.50 | 72.50 | 72.50 | 72.50 | 72.50 |
|  | a* | 1.93 | 1.93 | 1.93 | 1.93 | 1.93 | 1.93 | 1.93 | 1.93 | 1.93 | 1.93 |
|  | b* | 11.98 | 11.98 | 11.98 | 11.98 | 11.98 | 11.98 | 11.98 | 11.98 | 11.98 | 11.98 |
|  | Contrast Ratio | 0.47 | 0.81 | 0.43 | 0.84 | 0.53 | 0.75 | 0.45 | 0.79 | 0.50 | 0.95 |
|  | Thickness | 1.5 mm | 1.5 mm | 1.5 mm | 1.5 mm | 1.5 mm | 1.5 mm | 1.5 mm | 1.5 mm | 1.5 mm | 1.5 mm |
|  | Evaluation Result | A | AA | C | C | AA | AA | C | C | AA | AA |

TABLE 4

|  |  | Example 16 | Example 17 | Example 18 | Example 19 | Example 20 | Example 21 | Example 22 | Example 23 | Example 24 |
|---|---|---|---|---|---|---|---|---|---|---|
| A layer (W layer) | L* (WL) | 78.00 | 68.80 | 87.20 | 65.00 | 90.00 | 78.00 | 78.00 | 78.00 | 78.00 |
|  | a* (Wa) | 3.00 | 3.00 | 3.00 | 3.00 | 3.00 | −3.10 | 4.80 | −3.50 | 5.50 |
|  | b* (Wb) | 8.05 | 8.05 | 8.05 | 8.05 | 8.05 | 8.05 | 8.05 | 8.05 | 8.05 |
|  | Contrast Ratio | 0.42 | 0.42 | 0.42 | 0.42 | 0.42 | 0.42 | 0.42 | 0.42 | 0.42 |
|  | Thickness | 2.0 mm | 2.0 mm | 2.0 mm | 2.0 mm | 2.0 mm | 2.0 mm | 2.0 mm | 2.0 mm | 2.0 mm |
| C Layer (D layer) | L* (DL) | 55.00 | 55.00 | 55.00 | 55.00 | 55.00 | 55.00 | 55.00 | 55.00 | 55.00 |
|  | a* (Da) | 0.85 | 0.85 | 0.85 | 0.85 | 0.85 | 0.85 | 0.85 | 0.85 | 0.85 |
|  | b* (Db) | 15.90 | 15.90 | 15.90 | 15.90 | 15.90 | 15.90 | 15.90 | 15.90 | 15.90 |
|  | Contrast Ratio | 0.75 | 0.75 | 0.75 | 0.75 | 0.75 | 0.75 | 0.75 | 0.75 | 0.75 |
|  | Thickness | 6.5 mm | 6.5 mm | 6.5 mm | 6.5 mm | 6.5 mm | 6.5 mm | 6.5 mm | 6.5 mm | 6.5 mm |
| B layer (30% position layer) | L* | 66.50 | 61.90 | 71.10 | 60.00 | 72.50 | 66.50 | 66.50 | 66.50 | 66.50 |
|  | a* | 1.93 | 1.93 | 1.93 | 1.93 | 1.93 | −1.13 | 2.83 | −1.33 | 3.18 |
|  | b* | 11.98 | 11.98 | 11.98 | 11.98 | 11.98 | 11.98 | 11.98 | 11.98 | 11.98 |
|  | Contrast Ratio | 0.64 | 0.64 | 0.64 | 0.64 | 0.64 | 0.64 | 0.64 | 0.64 | 0.64 |
|  | Thickness | 1.5 mm | 1.5 mm | 1.5 mm | 1.5 mm | 1.5 mm | 1.5 mm | 1.5 mm | 1.5 mm | 1.5 mm |
|  | Evaluation Result | AA | AA | AA | B | A | A | AA | B | B |

TABLE 5

|  |  | Example 25 | Example 26 | Example 27 | Example 28 | Example 29 | Example 30 | Example 31 |
|---|---|---|---|---|---|---|---|---|
| A layer (W layer) | L* (WL) | 78.00 | 78.00 | 78.00 | 78.00 | 87.20 | 78.00 | 87.20 |
|  | a* (Wa) | 3.00 | 3.00 | 3.00 | 3.00 | 3.00 | 3.00 | 3.00 |
|  | b* (Wb) | −2.90 | 19.00 | −3.50 | 20.00 | 8.05 | 8.05 | 8.05 |
|  | Contrast Ratio | 0.42 | 0.42 | 0.42 | 0.42 | 0.42 | 0.42 | 0.42 |
|  | Thickness | 2.0 mm | 2.0 mm | 2.0 mm | 2.0 mm | 2.0 mm | 2.0 mm | 2.0 mm |
| C Layer (D layer) | L* (DL) | 55.00 | 55.00 | 55.00 | 55.00 | 79.00 | 50.00 | 85.00 |
|  | a* (Da) | 0.85 | 0.85 | 0.85 | 0.85 | 0.85 | 0.85 | 0.85 |
|  | b* (Db) | 15.90 | 15.90 | 15.90 | 15.90 | 15.90 | 15.90 | 15.90 |
|  | Contrast Ratio | 0.75 | 0.75 | 0.75 | 0.75 | 0.75 | 0.75 | 0.75 |
|  | Thickness | 6.5 mm | 6.5 mm | 6.5 mm | 6.5 mm | 6.5 mm | 6.5 mm | 6.5 mm |
| B layer (30% position layer) | L* | 66.50 | 66.50 | 66.50 | 66.50 | 83.10 | 64.00 | 86.10 |
|  | a* | 1.93 | 1.93 | 1.93 | 1.93 | 1.93 | 1.93 | 1.93 |
|  | b* | 6.50 | 17.45 | 6.20 | 17.95 | 11.98 | 11.98 | 11.98 |
|  | Contrast Ratio | 0.64 | 0.64 | 0.64 | 0.64 | 0.64 | 0.64 | 0.64 |
|  | Thickness | 1.5 mm | 1.5 mm | 1.5 mm | 1.5 mm | 1.5 mm | 1.5 mm | 1.5 mm |
|  | Evaluation Result | AA | A | A | B | AA | B | B |

TABLE 6

|  |  | Example 32 | Example 33 | Example 34 | Example 35 | Example 36 | Example 37 | Example 38 | Example 39 |
|---|---|---|---|---|---|---|---|---|---|
| A layer (W layer) | L* (WL) | 78.00 | 78.00 | 78.00 | 78.00 | 78.00 | 78.00 | 78.00 | 78.00 |
|  | a* (Wa) | 3.00 | 3.00 | 3.00 | 3.00 | 3.00 | 3.00 | 3.00 | 3.00 |
|  | b* (Wb) | 8.05 | 8.05 | 8.05 | 8.05 | 8.05 | 8.05 | 8.05 | 8.05 |
|  | Contrast Ratio | 0.42 | 0.42 | 0.42 | 0.42 | 0.42 | 0.42 | 0.42 | 0.42 |
|  | Thickness | 2.0 mm | 2.0 mm | 2.0 mm | 2.0 mm | 2.0 mm | 2.0 mm | 2.0 mm | 2.0 mm |

TABLE 6-continued

|  |  | Example 32 | Example 33 | Example 34 | Example 35 | Example 36 | Example 37 | Example 38 | Example 39 |
|---|---|---|---|---|---|---|---|---|---|
| C Layer (D layer) | L* (DL) | 55.00 | 55.00 | 55.00 | 55.00 | 55.00 | 55.00 | 55.00 | 55.00 |
|  | a* (Da) | −4.60 | 10.60 | −5.00 | 11.00 | 0.85 | 0.85 | 0.85 | 0.85 |
|  | b* (Db) | 15.90 | 15.90 | 15.90 | 15.90 | 2.50 | 29.30 | 2.00 | 30.00 |
|  | Contrast Ratio | 0.75 | 0.75 | 0.75 | 0.75 | 0.75 | 0.75 | 0.75 | 0.75 |
|  | Thickness | 6.5 mm | 6.5 mm | 6.5 mm | 6.5 mm | 6.5 mm | 6.5 mm | 6.5 mm | 6.5 mm |
| B layer (30% position layer) | L* | 66.50 | 66.50 | 66.50 | 66.50 | 66.50 | 66.50 | 66.50 | 66.50 |
|  | a* | −0.80 | 6.80 | −1.00 | 7.00 | 1.93 | 1.93 | 1.93 | 1.93 |
|  | b* | 11.98 | 11.98 | 11.98 | 11.98 | 5.28 | 18.68 | 5.03 | 19.03 |
|  | Contrast Ratio | 0.64 | 0.64 | 0.64 | 0.64 | 0.64 | 0.64 | 0.64 | 0.64 |
|  | Thickness | 1.5 mm | 1.5 mm | 1.5 mm | 1.5 mm | 1.5 mm | 1.5 mm | 1.5 mm | 1.5 mm |
|  | Evaluation Result | AA | A | A | B | A | AA | B | A |

TABLE 7

|  |  | Example 40 | Example 41 | Example 42 | Example 43 | Example 44 | Example 45 | Example 46 | Example 47 |
|---|---|---|---|---|---|---|---|---|---|
| A layer (W layer) | L* (WL) | 78.00 | 87.20 | 78.00 | 87.20 | 78.00 | 78.00 | 78.00 | 78.00 |
|  | a* (Wa) | 3.00 | 3.00 | 3.00 | 3.00 | −3.10 | 4.80 | −3.10 | 4.80 |
|  | b* (Wb) | 8.05 | 8.05 | 8.05 | 8.05 | 8.05 | 8.05 | 8.05 | 8.05 |
|  | Contrast Ratio | 0.42 | 0.42 | 0.42 | 0.42 | 0.42 | 0.42 | 0.42 | 0.42 |
|  | Thickness | 2.0 mm | 2.0 mm | 2.0 mm | 2.0 mm | 2.0 mm | 2.0 mm | 2.0 mm | 2.0 mm |
| C Layer (D layer) | L* (DL) | 55.00 | 79.00 | 55.00 | 79.00 | 55.00 | 55.00 | 55.00 | 55.00 |
|  | a* (Da) | 0.85 | 0.85 | 0.85 | 0.85 | −4.60 | 10.60 | −4.60 | 10.60 |
|  | b* (Db) | 15.90 | 15.90 | 15.90 | 15.90 | 15.90 | 15.90 | 15.90 | 15.90 |
|  | Contrast Ratio | 0.75 | 0.75 | 0.75 | 0.75 | 0.75 | 0.75 | 0.75 | 0.75 |
|  | Thickness | 6.5 mm | 6.5 mm | 6.5 mm | 6.5 mm | 6.5 mm | 6.5 mm | 6.5 mm | 6.5 mm |
| B layer (30% position layer) | L* | 61.90 | 83.10 | 61.00 | 84.00 | 66.50 | 66.50 | 66.50 | 66.50 |
|  | a* | 1.93 | 1.93 | 1.93 | 1.93 | −3.85 | 7.70 | −4.00 | 8.00 |
|  | b* | 11.98 | 11.98 | 11.98 | 11.98 | 11.98 | 11.98 | 11.98 | 11.98 |
|  | Contrast Ratio | 0.64 | 0.64 | 0.64 | 0.64 | 0.64 | 0.64 | 0.64 | 0.64 |
|  | Thickness | 1.5 mm | 1.5 mm | 1.5 mm | 1.5 mm | 1.5 mm | 1.5 mm | 1.5 mm | 1.5 mm |
|  | Evaluation Result | AA | AA | A | A | AA | A | A | B |

TABLE 8

|  |  | Example 48 | Example 49 | Example 50 | Example 51 |
|---|---|---|---|---|---|
| A layer (W layer) | L* (WL) | 78.00 | 78.00 | 78.00 | 78.00 |
|  | a* (Wa) | 3.00 | 3.00 | 3.00 | 3.00 |
|  | b* (Wb) | 2.50 | 19.00 | 2.50 | 19.00 |
|  | Contrast Ratio | 0.42 | 0.42 | 0.42 | 0.42 |
|  | Thickness | 2.0 mm | 2.0 mm | 2.0 mm | 2.0 mm |
| C Layer (D layer) | L* (DL) | 55.00 | 55.00 | 55.00 | 55.00 |
|  | a* (Da) | 0.85 | 0.85 | 0.85 | 0.85 |
|  | b* (Db) | 2.90 | 29.30 | 2.90 | 29.30 |
|  | Contrast Ratio | 0.75 | 0.75 | 0.75 | 0.75 |
|  | Thickness | 6.5 mm | 6.5 mm | 6.5 mm | 6.5 mm |
| B layer (30% position layer) | L* | 66.50 | 66.50 | 66.50 | 66.50 |
|  | a* | 1.93 | 1.93 | 1.93 | 1.93 |
|  | b* | 2.70 | 24.15 | 2.60 | 25.00 |
|  | Contrast Ratio | 0.64 | 0.64 | 0.64 | 0.64 |
|  | Thickness | 1.5 mm | 1.5 mm | 1.5 mm | 1.5 mm |
|  | Evaluation Result | AA | AA | A | A |

TABLE 9

|  |  | Example 52 | Example 53 | Example 54 | Example 55 | Example 56 | Example 57 | Example 58 | Example 59 |
|---|---|---|---|---|---|---|---|---|---|
| A layer (W layer) | L* (WL) | 78.00 | 78.00 | 78.00 | 78.00 | 78.00 | 78.00 | 78.00 | 78.00 |
|  | a* (Wa) | 3.00 | 3.00 | 3.00 | 3.00 | 3.00 | 3.00 | 3.00 | 3.00 |
|  | b* (Wb) | 8.05 | 8.05 | 8.05 | 8.05 | 8.05 | 8.05 | 8.05 | 8.05 |
|  | Contrast Ratio | 0.42 | 0.42 | 0.42 | 0.42 | 0.42 | 0.42 | 0.42 | 0.42 |
|  | Thickness | 1.5 mm | 3.0 mm | 1.0 mm | 3.5 mm | 2.0 mm | 2.0 mm | 2.0 mm | 2.0 mm |
| C Layer (D layer) | L* (DL) | 67.00 | 67.00 | 67.00 | 67.00 | 67.00 | 67.00 | 67.00 | 67.00 |
|  | a* (Da) | 0.85 | 0.85 | 0.85 | 0.85 | 0.85 | 0.85 | 0.85 | 0.85 |
|  | b* (Db) | 15.90 | 15.90 | 15.90 | 15.90 | 15.90 | 15.90 | 15.90 | 15.90 |
|  | Contrast Ratio | 0.75 | 0.75 | 0.75 | 0.75 | 0.75 | 0.75 | 0.75 | 0.75 |
|  | Thickness | 7.0 mm | 5.5 mm | 7.5 mm | 5.0 mm | 7.0 mm | 6.0 mm | 7.5 mm | 5.5 mm |
| B layer (30% position layer) | L* | 72.50 | 72.50 | 72.50 | 72.50 | 72.50 | 72.50 | 72.50 | 72.50 |
|  | a* | 1.93 | 1.93 | 1.93 | 1.93 | 1.93 | 1.93 | 1.93 | 1.93 |
|  | b* | 11.98 | 11.98 | 11.98 | 11.98 | 11.98 | 11.98 | 11.98 | 11.98 |
|  | Contrast Ratio | 0.64 | 0.64 | 0.64 | 0.64 | 0.64 | 0.64 | 0.64 | 0.64 |
|  | Thickness | 1.5 mm | 1.5 mm | 1.5 mm | 1.5 mm | 1.0 mm | 2.0 mm | 0.5 mm | 2.5 mm |
|  | Evaluation Result | AA | AA | A | A | AA | AA | A | A |

With respect to the use of substantially any plural and/or singular terms herein, those having skill in the art can translate from the plural to the singular and/or from the singular to the plural as is appropriate to the context.

INDUSTRIAL APPLICABILITY

The dental mill blank of the present disclosure may be used for a block or a disk which are used for preparation of a dental crown restoration by cutting and machining using CAD/CAM technique in the dental field.

DESCRIPTION OF THE REFERENCE NUMERALS

A: First layer, W layer (enamel color layer)
B: Second layer
C: Third layer, D layer (cervical area color layer)
F: Dental crown form
G1: G1 layer
G2: G2 layer

What is claimed is:

1. A dental mill blank including three or more layers which are stacked on each other, wherein
    in a case in which a chromaticity of each layer based on a $L^*a^*b^*$ colorimetric system is expressed by $\sqrt{(L^{*2} \times a^{*2} \times b^{*2})}$, a layer which has the highest chromaticity is defined as a W layer, wherein chromaticities in the W layer based on the $L^*a^*b^*$ colorimetric system are expressed by WL, Wa, and Wb, and a layer which has the lowest chromaticity is defined as a D layer, wherein chromaticities in the D layer based on the $L^*a^*b^*$ colorimetric system are expressed by DL, Da, and Db,
    the W layer and the D layer are respectively disposed on opposed surface layers of the dental mill blank,
    a color of a 30% position layer, wherein chromaticities in the 30% position layer based on the $L^*a^*b^*$ colorimetric system are expressed by 30% position L, 30% position a, and 30% position b, which includes a position spaced from a surface of the dental mill blank of a W layer-side by 30% of a dimension between the surface of the dental mill blank of a W layer-side and a surface of the dental mill blank of a D layer-side, wherein when a boundary of the layers is positioned at the position spaced from the surface of the dental mill blank of the W layer-side by 30%, wherein the 30% position layer includes a position exceeding the position spaced from the surface of the dental mill blank of the W layer-side by 30% satisfies the following relations:

30% position $L$ is within a range of $((WL+DL)/2) \times$ (0.90 to 1.10),

30% position $a$ is within a range of $((Wa+Da)/2) \times$ (0.90 to 1.10), and

30% position $b$ is within a range of $((Wb+Db)/2) \times$ (0.90 to 1.10), a contrast ratio of the D layer is within a range of 0.55 to 0.95, and
    a contrast ratio of the 30% position layer is within a range of the contrast ratio of the D layer $\times$ (0.70 to 1.00).

2. The dental mill blank according to claim 1, wherein the contrast ratio of the 30% position layer is within a range of 0.50 to 0.95.

3. The dental mill blank according to claim 1, wherein the W layer is positioned from the surface of the dental mill blank of the W layer-side to a position spaced from the surface of the dental mill blank of the W layer-side by 15 to 30% of the dimension between the surface of the dental mill blank of the W layer-side and the surface of the dental mill blank of the D layer-side,
    a thickness of the 30% position layer is within a range of 10 to 20% of the dimension between the surface of the dental mill blank of the W layer-side and the surface of the dental mill blank of the D layer-side, and
    the 30% position layer is positioned adjacent to the W layer.

4. The dental mill blank according to claim 1, wherein a color of each layer satisfies the following relations:
WL is within a range of 68.8 to 87.2
Wa is within a range of −3.1 to 4.8
Wb is within a range of −2.9 to 19.0
DL is within a range of 55.0 to 79.0
Da is −4.6 or more
Db is 29.3 or less
30% position L is within a range of 61.9 to 83.1
30% position a is −3.85 or more
30% position b is within a range of 2.7 to 24.15
DL<30% position L<WL
Da<30% position a<Wa and
Db>30% position b>Wb.

* * * * *